(12) United States Patent
Sarussi

(10) Patent No.: US 7,359,741 B2
(45) Date of Patent: Apr. 15, 2008

(54) SENSOR AND RADIANCE BASED DIAGNOSTICS

(75) Inventor: Israel Sarussi, Mobile Mail Hof Aza (IL)

(73) Assignee: SPO Medical Equipment Ltd., Kfar Saba (IL)

( * ) Notice: Subject to any disclaimer, the term of this patent is extended or adjusted under 35 U.S.C. 154(b) by 2 days.

(21) Appl. No.: 11/296,389

(22) Filed: Dec. 8, 2005

(65) Prior Publication Data

US 2006/0089547 A1    Apr. 27, 2006

Related U.S. Application Data

(63) Continuation of application No. 09/831,944, filed on Dec. 12, 2001, now Pat. No. 7,006,855.

(51) Int. Cl.
*A61B 5/1455*    (2006.01)
(52) U.S. Cl. .................................................. 600/310
(58) Field of Classification Search ............. 600/310, 600/322, 323, 324, 340, 344
See application file for complete search history.

(56) References Cited

U.S. PATENT DOCUMENTS 5,025,791 A * 6/1991 Niwa ........................... 600/324
5,427,093 A * 6/1995 Ogawa et al. ............... 600/323
5,797,841 A * 8/1998 Delonzor et al. ............ 600/323
7,006,855 B1 * 2/2006 Sarussi ........................ 600/310

* cited by examiner

*Primary Examiner*—Eric F Winakur
(74) *Attorney, Agent, or Firm*—Henry M. Sinai; (IP-Partnership)

(57) ABSTRACT

The present invention provides a sensor for radiance based diagnostics of body tissues comprising a performing component and an adhering component, the performing component comprising at least one radiance source for radiating a tissue and at least one detector for detecting rays emitted from the radiance source. The adhering component is capable of fastening the performing component to a tissue such that the radiance source and detector are facing and contiguous with the tissue, and such that when operative, the adhering component hermetically fastens the performing component to the tissue to the extent that the detector only receives rays which are reflected from within the tissue. The sensor may include a controlling device which senses external conditions and which is capable of controlling the sensor in response to the sensed conditions. The sensor may also be in communication with an electronic circuit, which may control the radiance source and/or detector and perform analysis of the data received by the detector.

14 Claims, 3 Drawing Sheets

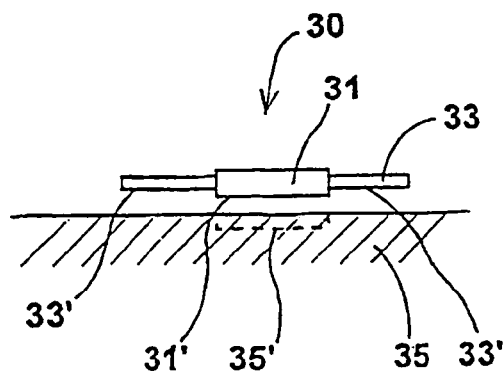
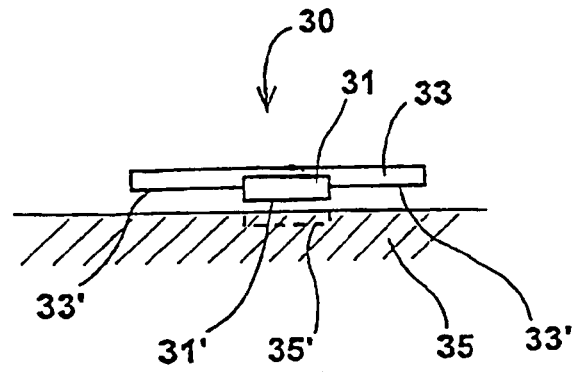
Fig. 3A
Fig. 3B
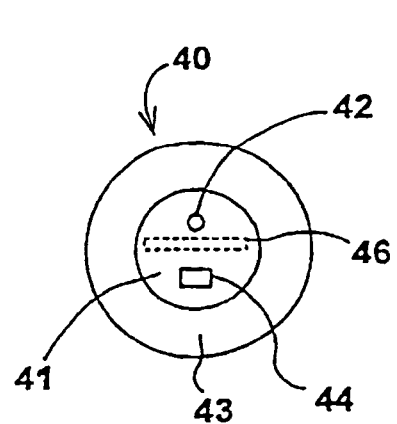
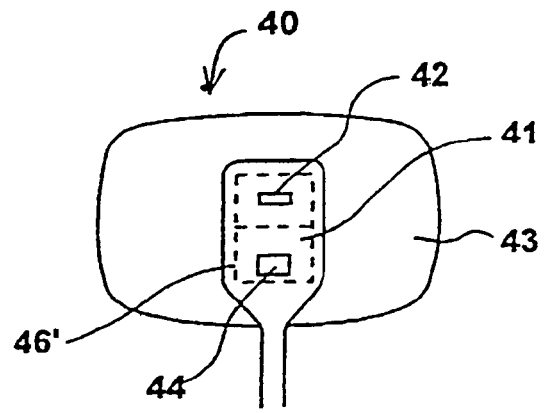
Fig. 4A
Fig. 4B

FIG. 5A
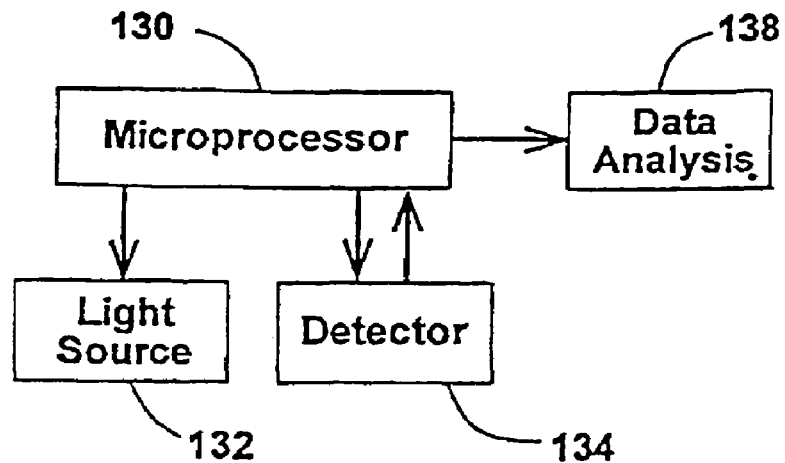
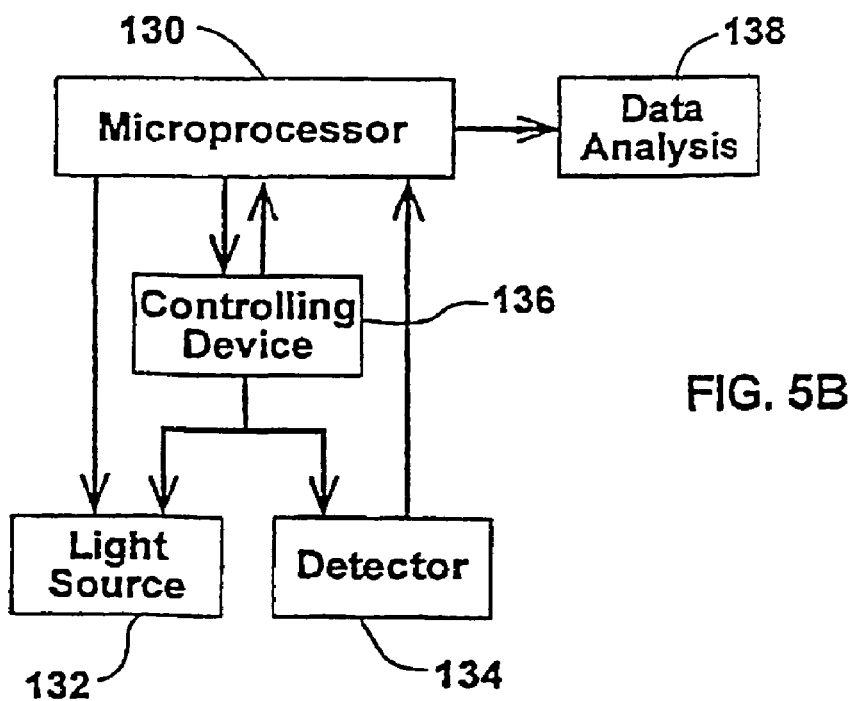
FIG. 5B

SENSOR AND RADIANCE BASED DIAGNOSTICS

RELATED APPLICATIONS

This application is a continuation application of U.S. application Ser. No. 09/831,944; filed Dec. 12, 2001 now U.S. Pat. No. 7,006,855.

FIELD OF THE INVENTION

The present invention relates to a sensor and system for radiance based diagnostics of body tissues and to a method for radiance based diagnostics of body tissues.

BACKGROUND OF THE INVENTION

Radiance based diagnostics of body tissues involves radiating a body tissue and obtaining data relating to the transmittance or reflection of the radiated light from the tissue, for analysis of tissue constituents. For example, electro-optical measurement of blood characteristics has been found to be useful in many areas of blood constituent diagnostics, such as glucose levels, oxygen saturation, hematocrit, bilirubin and others. Pulse oximetry is a method for measuring oxygen saturation in the blood, in which two or more wavelengths are radiated through an organ at a point where blood perfuses the organ. Reflective pulse oximetry employs at least one light source and a least one detector which are placed at the same side of an organ. The light source is for radiating the organ and the detector is for receiving the light reflected from the organ. The reflected light is analyzed for measuring the percent of saturated oxygen in the blood.

These methods of body tissue diagnostics usually employ sensors, which are placed on body tissues, and which comprise at least one radiance source for radiating the tissue and at least one radiance detector, for detecting the rays transmitted through or reflected from the tissue. The accuracy of the results obtained in these methods depends, to a great extent, on ensuring that the detector, or detectors, is exposed only to rays which have passed through the examined tissue and not to other rays, such as rays coming directly form the radiance source.

When a sensor is placed on body tissues, especially on stretched tissues (such as over a bone), or due to irregular tissue surface (such as in wrinkles), there might be a small space between the face of the sensor and the tissue, through which some of the rays can pass directly from the radiance source to the detector, thereby adversely affecting the measurement.

Reference is now made to FIG. 1 which is a schematic side view illustration of a prior art sensor. The sensor, generally referenced 10, contains a light source 12 and a light detector 14. The sensor is placed onto examined tissue 16 and, when operated, light is radiated from light source 12 onto tissue 16. Depending on how the light source 12 is directed, most of the light will pass through the tissue 16 and be partly reflected from the tissue. The reflected light 14' will be received by detector 14 to be analyzed. However, a small fraction of the light 18' radiated from the light source 12 will not pass through the tissue 16 but pass directly to the detector 14, through the small space 18 between the sensor 10 and the tissue 16. Since the detector can not differentiate between the two lights, 14' and 18', the analysis results will be inaccurate.

SUMMARY OF THE INVENTION

It is an object of the present invention to provide a sensor for radiance based diagnostics of body tissues, which ensures that only light which has passed through an examined tissue is received by the sensor's detector.

The sensor, which is placed on an examined tissue, comprises a performing component and an adhering component. The performing component, which consists of at least one radiance source for radiating a tissue and at least one detector for detecting the rays reflected from within the tissue, protrudes from the plane of the adhering component, in the direction of the examined tissue, when being placed on the tissue. The adhering component is capable of fastening the performing component to the examined tissue. The adhering component may be a tape of any suitable adhering material, which forms a frame around the performing component or, the adhering component may be a tape which overlays the performing component, and which, when being fastened to an examined tissue, covers the performing component, fastening it to the underlying tissue.

The design of the sensor, as described above, ensures that, when the adhering component is placed in contact with the tissue, the performing component presses into the tissue in such a way that the radiance source and detector are hermetically sealed off from each other by the tissue, thus, when the sensor is operated, only rays from the radiance source, which have passed through the examined tissue and reflected therefrom will be received by the detector. External light and direct light from the radiance source are excluded and thus the accuracy of the measurements is greatly increased.

In one embodiment of the invention, especially useful for reflective oximetry, the performing component further comprises a raised partition in between the radiance source and the detector, or a wall surrounding either the radiance source or the detector, or both, while separating them from each other. The partition or wall assists in sealing off the detector from the radiance source, to further ensure that no light is received by the detector, directly from the radiance source.

In another embodiment, the sensor includes a controlling device which senses external conditions and which is capable of responding to the sensed conditions, such as by arresting the sensor operation when the external conditions indicate inaccurate operation of the sensor. For example, the controlling device may be a pressure or proximity detector that will enable sensor operation only when it senses the required proximity to the examined tissue or a pressure which indicates that the performing component is sufficiently pressed on to the examined tissue.

It is further an object of the present invention to provide a system for radiance based diagnostics of body tissues. The system comprises a sensor and a microprocessor that is in electronic communication with a component of the sensor.

The sensor comprises a performing component consisting of at least one radiance source for radiating a tissue and at least one detector for detecting the rays transmitted through or reflected from the tissue, and an adhering component that is capable of fastening the performing component to an examined body tissue. The microprocessor is in electronic communication with the performing component of the sensor for controlling the radiance source and the detector, and for performing analysis of the data received by the detector.

The sensor may also comprise a controlling device that senses external conditions. The controlling device may be in communication with the microprocessor, providing information to the microprocessor which contributes to its operation of controlling the radiance source and detector. Alternatively, the controlling device may be in direct communication with the radiance source and/or detector, for controlling their operation in accordance with the sensed external conditions.

It is another object of the present invention to provide a method for radiance based analysis of body tissues. The method comprises the steps of fastening the sensor of the invention to an examined tissue, thereby to hermetically fasten the performing component to the body tissue; radiating the body tissue and detecting the light reflected from within tissue; and obtaining and analyzing data from the sensor. The sensor is configured to exclude external light and direct light from the radiance source.

BRIEF DESCRIPTION OF THE FIGURES

The present invention will be understood and appreciated more fully from the following detailed description taken in conjunction with the drawings in which:

FIGS. 3A and 3B are schematic side views of the sensors of FIGS. 2A and 2B, respectively, operable according to an embodiment of the present invention;

FIGS. 4A and 4B are schematic under views of the sensors of FIGS. 2A and 2B, respectively, according to another embodiment of the present invention; and FIGS. 5A and 5B are block diagram illustrations of the operation of a system including the sensors of FIGS. 2A and 2B and the sensor of FIG. 2C, correspondingly.

DETAILED DESCRIPTION OF THE INVENTION

The present invention relates to a sensor for radiance based diagnostics of body tissues, which ensures that only light from a radiance source, which has passed through an examined tissue, is received by the sensor's detector, thereby ensuring higher accuracy of results.

The invention will be described in reference to reflective pulse oximetry, but it will be appreciated by persons skilled in the art, that the invention relates to any radiance based method of diagnosing body tissues, reflective or other. The radiance source and detector, may, therefore, be situated on the same side of the examined tissue or on opposing sides, according to the diagnostic method used. The terms "radiance source" and "detector", in the present invention, relate to one or more radiance source or detector. Furthermore, the term "radiance source", in the present invention, refers to a radiance source which is not limited to visible light but may radiate in any wavelength which is suitable for the specific method used.

Figure 1:
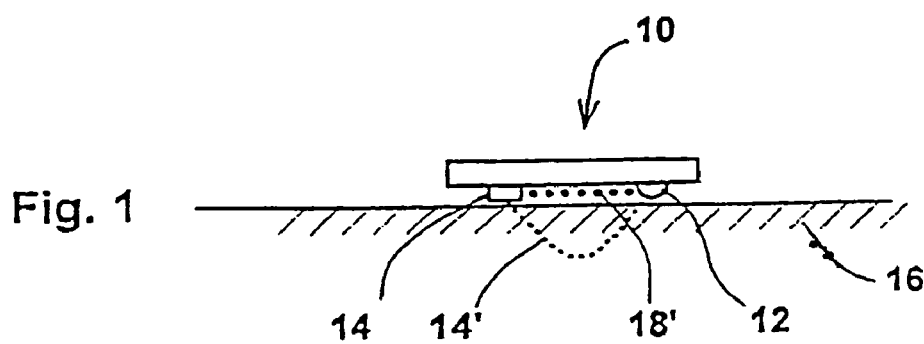
FIG. 1 is a schematic side view of a prior art sensor.
Figure 2A:
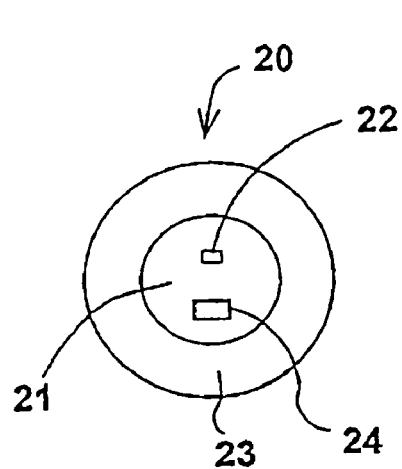
FIGS. 2A and 2B are schematic under views of the sensor according to two embodiments of the present invention.
Figure 2B:
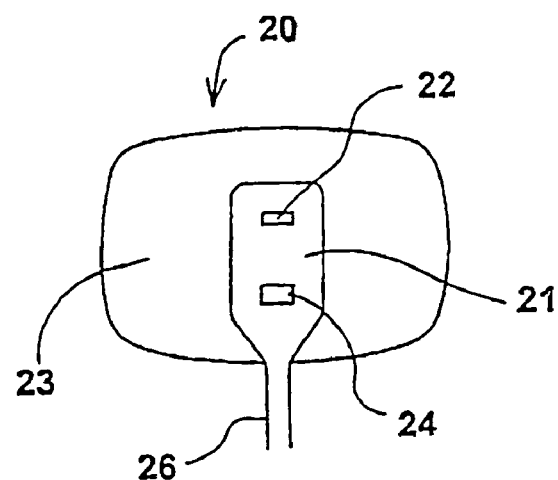
Figure 2C:
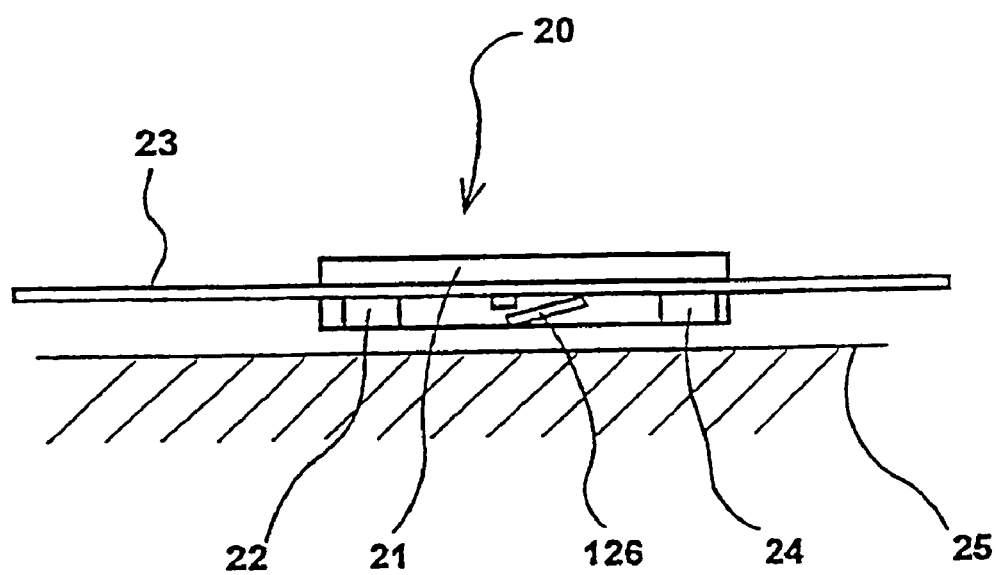
FIG. 2C is a schematic side view of the sensor according to another embodiment of the present invention.

Reference is now made to FIGS. 2A, 2B and 2C, which are schematic under views (FIGS. 2A and 2B) and side view (FIG. 2C) of a sensor, generally referenced 20. The sensor 20 comprises a performing component 21 and an adhering component 23. The performing component 21 consists of a radiance source 22 for radiating a tissue and detector 24 for detecting the rays reflected from the tissue. The whole performing component 21, or parts of it (such as the radiance source 22 and/or detector 24), protrude from the plane of the adhering component 23.

The adhering component 23 is a tape for fastening the performing component to an examined body tissue, and for keeping it in place. In FIGS. 2A and 2C, the adhering component 23 is an adhesive tape forming a frame around the performing component 21, which contacts both the performing component and underlying tissue. In FIG. 2B the adhering component 23 is a tape, i.e. made of stretchable material, which overlays the performing component, and which, when being fastened to a body tissue, covers the performing component, fastening it to the underlying tissue. The adhering component 23 may be disposable. It will be appreciated that the adhering component may also be formed as part of the performing component such as a band of adhesive material formed on the surface of the performing component meant to contact and adhere to the examined tissue.

The adhering component 23 is configured to hermetically fasten the performing component 21 to the tissue such that the radiance source 22 and the detector are facing and contiguous with the tissue. The adhering component 23 compresses the tissue so that external light and any direct light from the radiance source itself 22 is excluded. The detector 24 is effectively sealed off from the radiance source 22 so that rays emitted from the radiance source 22 are unable to reach the detector 24 through any other medium except from the tissue itself. Furthermore, by effectively fastening the performing component 21 to the tissue as well as sealing off the detector 24 from the radiance source 22, light reflected from the skin surface is reduced substantially and may be excluded all together, thereby allowing the detector 24 to more accurately measure the rays reflected from within the tissue, that is the rays which have passed through the examined tissue The performing component 21 may be powered through a cable 26 (shown only in FIG. 2B). Alternatively, the sensor 20 may be wireless and operated on a battery.

The embodiment described in FIG. 2C further comprises a controlling device 126 that may be in communication with either detector 24 or radiance source 22 or both. Controlling device 126 is capable of sensing external conditions and responding to these conditions. A detailed description of controlling device 126 is provided in the description of FIG. 5B.

Reference is now made to FIGS. 3A and 3B which are schematic side view illustrations of a sensor operable according to the invention. When the sensor, generally referenced 30, is placed on a body tissue 35, such that the adhering component 33 is placed in contact with the tissue 35, the performing component 31, which protrudes from the plane of the adhering component 33, in the direction of the tissue 35, presses into the tissue 35, forming indentation 35'. Adhering component 33 is in contact with performing component 31, such that, the adhering component surface 33' is essentially parallel to the performing component surface 31'. Accordingly, when sensor 30 is fastened to tissue 35, there is essentially no space between the adhering component 33, and the tissue 35. This ensures that the performing component 31 is pressed onto tissue 35 such that light cannot reach the detector either from the outside or directly from the radiance source.

The pressure exerted by performing component 31 on the tissue, fastens the radiance source and detector (not shown) to the tissue so that rays emitted from the radiance source, are unable to reach the detector through any other medium, but the tissue. Light reflected from the skin surface is reduced substantially and may be excluded all together, thereby allowing the sensor 30 to more accurately measure the rays reflected from within the tissue.

The performing component surface 31' can be coated or overlaid with a soft layer, such as a silicone or sponge layer. The soft layer, which does not overlay the radiance source or detector, will contribute to sealing off of the radiance source from the detector when the sensor is pressed onto the tissue 35.

Reference is now made to FIGS. 4A and 4B which are schematic under view illustrations of a sensor, generally referenced 40, according to another embodiment of the invention. In this embodiment, which is especially suitable for use in reflective oximetry, the performing component 41 of the sensor 40 comprises a raised partition 46 in between the radiance source 42 and the detector 44. The sensor 40 may also comprise a wall 46' surrounding either the radiance source 42 or the detector 44, or both, while separating them from each other (shown in FIG. 4B). When sensor 40 is fastened to a body tissue (as described in FIGS. 3A and 3B) by adhering component 43, partition 46 or wall 46', which are raised above the plane of the sensor 40, exert pressure on the tissue and thus seal off the detector 44 from the radiance source 42. Light reflected from the skin surface is reduced substantially and may be excluded all together, thereby allowing the sensor 40 to more accurately measure the rays reflected from within the tissue.

Reference is now made to FIG. 5A, which is a block diagram illustration of the operation of a system for radiance based diagnostics of body tissues, which includes the sensors 20 of FIGS. 2A and 2B. The system comprises an electronic circuit i.e., microprocessor 130 that is in electronic communication with the performing component of sensor 20 which includes radiance source 132 and detector 134. Microprocessor 130 controls radiance source 132 and/or detector 134 operation. Detector 134 provides microprocessor 130 with data relating to the light detected by it. Microprocessor 130 performs data analysis 138 which may include saving the data and/or further processing it and, optionally, displaying the processed data. Data analysis 138 may be performed in the same physical unit of microprocessor 130 or in a separate unit which is in communication with microprocessor 130. The processed data may further effect microprocessor 130 operation. Thus the microprocessor 130 operation may be fine tuned in accordance with the conditions prevailing in the examined tissue, as they are interpreted by the data analysis function of the microprocessor.

It will be appreciated that the term "microprocessor" relates to an electronic circuit capable of communicating with and/or controlling sensor components as described.

FIG. 5B is a block diagram illustration of a system for radiance based diagnostics of body tissues that includes the sensor 20 of FIG. 2C. This sensor includes controlling device 136 that may be in communication with microprocessor 130, on one hand and with radiance source 132 and detector 134, on the other hand, and through which microprocessor 130 may control the operation of the radiance source 132 and detector 134.

Controlling device 136 responds to external conditions, such as external pressure or external temperature, and may inform microprocessor 130 of these conditions. Microprocessor 130 may be programmed to differentially operate according to different external conditions. For example, controlling device 136 may function to alert microprocessor 130 of the fact that there is insufficient pressure or proximity to the examined tissue, and according to the programmed parameters, microprocessor 130 may either stop sensor 20 operations, or alert an operator by displaying this fact, through data analysis 138.

Alternatively, controlling device 136 may be a switch which responds to pressure or proximity to the examined tissue 35 (see FIGS. 3A and 3B). Thus, when the performing component 21, or parts of it, are sufficiently pressed to examined tissue 35, so as to ensure that only light from radiance source 132 that has passed through the examined tissue 35, will be detected by detector 134, the controlling device 136 will be in the ON indication, either enabling microprocessor 130 operation or enabling communication between the microprocessor 130 and radiance source 132 and detector. When insufficient pressure or proximity, between the performing component and the examined tissue, is detected by controlling device 136, it will be in the OFF indication, thereby either arresting microprocessor 130 operation or disconnecting the communication between the microprocessor 130 and radiance source 132 and detector 134. Thus the controlling device 136 contributes to the sensor 20 efficiency.

The controlling device 136 may also respond to other external parameters, such as the examined tissue temperature. Thus, the controlling device 136 will either alert an operator, disconnect the microprocessor or disconnect communication between the microprocessor and the performing component, if is senses a temperature different from that of a preprogrammed temperature, such as the body temperature. The sensor 20, which may need to be placed on the examined tissue 35 for a long period, such as over night, may heedlessly fall off the examined tissue 35 and be pressed on to the patient's bed, instead of onto his body. The microprocessor 130 will be alerted to this fact by the controlling device 136, and act accordingly, as described above.

The controlling device 136 may additionally function to ensure that the microprocessor 130 is operative only with the appropriate sensor 20. For example, sensor 20 can include a controlling device 136 that is a pressure detector that is in the OFF indication for the time it takes to achieve appropriate pressure between the sensor and the examined tissue. Accordingly, microprocessor 130 can be programmed to operate only after being shut off for a predetermined period (which would be, for example, the time it takes to achieve appropriate pressure between the sensor and examined tissue). Thus, a sensor 20 that does not include a controlling device 136 will not be operative with the programmed microprocessor 130.

Both in FIG. 5A and in FIG. 5B, the microprocessor 130 control of the sensor 20 components (radiance source 132 and/or detector 134) may be achieved through connecting wires or by remote control, such as by utilizing radiant energy. Thus the microprocessor 130 may be in close contact with the sensor 20, situated close to the patient's body, or the microprocessor 130 may be at some distance from the sensor 20.

It will be appreciated by persons skilled in the art that the present invention is not limited by what has been particularly shown and described herein above. Rather the scope of the invention is defined by the claims which follow:

I claim:

1. A sensor, for radiance based diagnostics, comprising a performing component and an adhering component,
   said performing component comprising:
   a lower and an upper surface;
   at least one radiance source for radiating a tissue; and
   at least one detector for detecting rays reflected from within said tissue;
   wherein said adhering component comprises a sealable lower surface having a greater surface area than the surface area of the performing component, said sealable lower surface configured to surround and adhesively adhere to the upper surface of the performing component, the lower surface of said performing component extending beyond the lower sealable surface of the adhering component;

wherein said performing component comprises means to block the detector from the radiance source so that rays emitted from the radiance source are unable to reach the detector through any other medium except reflected from the tissue;

wherein the lower sealable surface of the adhering component is adhesively attachable to the tissue to form an indentation in the tissue, the surface area of said indentation corresponding to the lower surface of the performing component, said indentation preventing external light from being detected by said at least one detector; and wherein said sensor further comprises a controlling device capable of sensing and responding to external conditions and capable of controlling sensor components operation said controlling device being a pressure or proximity detector configured to enable sensor operation only when the performing component is fastened to the tissue to the extent that the detector only receives rays which are reflected from the tissue.

2. A sensor according to claim 1 wherein the adhering component is a tape of adhering material framing the performing component and which, when fastening the performing component to the tissue, contacts the tissue.

3. A sensor according to claim 1 wherein the adhering component is a tape which, when fastening the performing component to the tissue, overlays the performing component and contacts the tissue.

4. A sensor according to claim 1 wherein the adhering component is formed as part of the performing component and contacts both the performing component and the tissue.

5. A sensor according to claim 1 wherein the performing component further comprises a partition in between the radiance source and the detector.

6. A sensor according to claim 5 wherein the partition further surrounds either radiance source or detector or both.

7. A system for radiance based diagnostics comprising a sensor and an electronic circuit in communication with the sensor components and capable of controlling the sensor components operation, said sensor comprising a performing component and an adhering component,:

said performing component comprising:
a lower and an upper surface;
at least one radiance source for radiating a tissue;
at least one detector for detecting rays reflected from said tissue; and
wherein said adhering component comprises a sealable lower surface having a greater surface area than the surface area of the performing component, said sealable lower surface configured to surround and adhesively adhere to the upper surface of the performing component, the lower surface of said performing component extending beyond the lower sealable surface of the adhering component;

wherein said performing component comprises means to block the detector from the radiance source so that rays emitted from the radiance source are unable to reach the detector through any other medium except reflected from the tissue;

wherein the lower sealable surface of the adhering component is adhesively attachable to the tissue to form an indentation in the tissue, the surface area of said indentation corresponding to the lower surface of the performing component, said indentation preventing external light from being detected by said at least one detector; and wherein the sensor further comprises a controlling device capable of sensing and responding to external conditions and which controlling device is capable of being in communication with sensor components, electronic circuit or both, wherein the controlling device is a pressure or proximity detector which enables operation of the sensor when the performing component is fastened to the tissue to the extent that the detector only receives rays which are reflected from the tissue.

8. A system according to claim 7 wherein the electronic circuit is in communication with and is capable of controlling the operation of either radiance source or detector or both.

9. A system according to claim 7 wherein the adhering component is a tape of adhering material framing the performing component and which, when fastening the performing component to the tissue, contacts the tissue.

10. A system according to claim 7 wherein the adhering component is a tape which, when fastening the performing component to the tissue, overlays the performing component and contacts the tissue.

11. A system according to claim 7 wherein the performing component further comprises a partition in between the radiance source and the detector, thereby to prevent light being received by the detector directly from the radiance source.

12. A system according to claim 11 wherein the partition further surrounds either radiance source or detector or both.

13. A system according to claim 7 wherein the electronic circuit controls the sensor component's operation.

14. A system according to claim 7 wherein the electronic circuit is programmed to operate in accordance with specific conditions communicated by the controlling device.

* * * * *